United States Patent [19]

Theeuwes

[11] 4,203,439
[45] May 20, 1980

[54] OSMOTIC SYSTEM WITH VOLUME AMPLIFIER FOR INCREASING AMOUNT OF AGENT DELIVERED THEREFROM

[75] Inventor: Felix Theeuwes, Los Altos, Calif.

[73] Assignee: Alza Corporation, Palo Alto, Calif.

[21] Appl. No.: 950,515

[22] Filed: Oct. 11, 1978

Related U.S. Application Data

[63] Continuation-in-part of Ser. No. 743,974, Nov. 22, 1976, abandoned.

[51] Int. Cl.² .............................................. A61M 31/00
[52] U.S. Cl. .................................. 128/260; 222/386.5
[58] Field of Search ....................... 128/260, 261, 268; 424/15, 16, 19, 44; 210/500 M; 222/386.5, 389

[56] References Cited

U.S. PATENT DOCUMENTS

| | | | |
|---|---|---|---|
| 3,444,290 | 5/1969 | Wai | 424/44 |
| 3,592,672 | 7/1971 | Rowley et al. | 210/500 M |
| 3,797,492 | 3/1974 | Place | 128/260 |
| 3,840,009 | 10/1974 | Michaels et al. | 128/260 |
| 3,845,770 | 11/1974 | Theeuwes et al. | 128/260 |
| 3,916,899 | 11/1975 | Theeuwes | 128/260 |
| 4,036,228 | 7/1977 | Theeuwes | 128/260 |

*Primary Examiner*—Robert W. Michell
*Assistant Examiner*—C. F. Rosenbaum
*Attorney, Agent, or Firm*—Paul L. Sabatine; Thomas E. Ciotti; Edward L. Mandell

[57] ABSTRACT

An osmotic system for delivering a beneficial agent is disclosed. The system comprises a wall surrounding a compartment and has a passageway through the wall for delivering agent from the compartment. The wall is formed of a material permeable to the passage of an external fluid and impermeable to the passage of agent. The compartment contains (1) an agent that is soluble in the fluid and exhibits an osmotic pressure gradient across the wall against the fluid, or (2) the compartment contains an agent having limited solubility in the fluid and exhibits a limited osmotic pressure gradient across the wall against the fluid. The compartment also contains along with (1) or (2) a volume amplifier for increasing the amount of agent delivered from the system. The amplifier comprises a membrane surrounding a gas generating couple with the membrane formed of an expandable material permeable to fluid and impermeable to the couple. In operation, agent is delivered from the system through the passageway at a controlled rate by fluid being imbibed through the wall into the compartment to produce a solution of (1), or a suspension of (2), and for imbibition by the amplifier causing the couple to generate gas and continuously fill the amplifier thereby urging it to increase in volume and fill the compartment whereby agent (1) or (2) is released at a rate controlled by the permeability of the wall, the osmotic pressure gradient across the wall, and the rate of imbibition and increase in volume of the amplifier over a prolonged period of time.

15 Claims, 6 Drawing Figures

OSMOTIC SYSTEM WITH VOLUME AMPLIFIER FOR INCREASING AMOUNT OF AGENT DELIVERED THEREFROM

CROSS-REFERENCE TO RELATED APPLICATION

This application is a continuation-in-part of U.S. patent application Ser. No. 743,974 filed on Nov. 22, 1976 now abandoned. This application and application Ser. No. 743,974 are both assigned to the ALZA Corporation of Palo Alto, California.

FIELD OF THE INVENTION

This invention pertains to an osmotic delivery system. More particularly, the invention relates to an osmotic system in the form of an osmotic device comprising a semipermeable wall surrounding a compartment containing an agent and a volume amplifier that produces an agent output of greater magnitude from the system over a prolonged period of time.

BACKGROUND OF THE INVENTION

Osmotic systems for delivering a beneficial agent to an environment of use are known to the art in U.S. Pat. Nos. 3,845,770 and 3,916,899. The systems disclosed in these patents comprise a semipermeable wall that surrounds a compartment containing an agent. The wall is permeable to an external fluid, substantially impermeable to agent, and there is a passageway through the wall for delivering the agent from the system. These systems release agent by fluid being imbibed through the wall into the compartment at a rate determined by the permeability of the wall and the osmotic pressure gradient across the wall to produce a solution of soluble agent, or a solution of an osmotic attractment containing an agent that has limited solubility in the fluid, which solution in either operation is dispensed from the system. These systems are extraordinarily effective for delivering both an agent that is soluble in the fluid, and for delivering an agent that has limited solubility in the fluid and is admixed with an osmotically effective compound that is soluble in the fluid and exhibits an osmotic pressure gradient across the wall against the fluid. While the above systems are outstanding and represent a pioneer advancement in the delivery art, and while they are endowed with ideal kinetics useful for delivering numerous beneficial agents, there is an occasional instance where the kinetics of the system can be unexpectedly improved to lead to more desirable results. For example, the rate of agent delivered by the system is constant for most agents as long as excess solid agent is present in the system with its rate declining parabolically toward zero as the agent's concentration decreases below saturation. That is, both the solubility and the density of the agent influence the amount of agent delivered at a constant rate, and that amount delivered at a declining rate is proportional to the solubility of the agent and inversely proportional to its density. These actions often make it difficult to deliver substantially all of the agent at a constant rate and thereby obtain the full benefit of the agent's therapeutic effect, particularly when the agent is very soluble or practically insoluble in the fluid and concomitantly a portion of the agent cannot be delivered at a constant rate. The present invention enhances the amount of these latter agents delivered at a constant and controlled rate over time by using a volume amplifier to improve kinetics and the amount of agent delivered from the system. The system with the amplifier also can optionally deliver increased amounts of very soluble or practically insoluble agents as pure agents substantially free of any osmotically effective compounds being mixed therewith. A mathematical presentation pertaining to the instant subject matter is known in *J. Pharm. Sci.*, Vol. 64, No. 12, pages 1987 to 1991, 1975.

OBJECTS OF THE INVENTION

Accordingly, it is an object of this invention to provide an improved osmotic system for the controlled delivery of an active agent over a prolonged period of time, which system overcomes the problems known to the prior art.

Another object of the invention is to provide an osmotic system that can deliver essentially all of its agent at a controlled and constant rate continuously over a prolonged period of time.

Another object of the invention is to provide an osmotic system for the delivery of a beneficial agent comprising a volume amplifier that improves the delivery kinetics of the system.

Still yet another object of the invention is to provide an osmotic system comprising a volume amplifier for increasing the amount of both very soluble or practically insoluble agents delivered from the system.

Still another object of the invention is to provide an osmotic system having a volume amplifier for uptaking fluid for maintaining excess solid agent in the solution or suspension for the controlled release of the agent over time.

Yet another object of the invention is to provide an osmotic system having a volume amplifier for continuously changing the internal volume in the compartment of the system thereby maintaining the solution or suspension in the system saturated with agent for constant release over time.

Another object of the invention is to provide an osmotic system for increasing the utility of short acting drugs and long acting drugs which because of their inherent physical and chemical properties, are difficult to dispense at a controlled and continuous rate, and which drugs can be dispensed with the system of this invention at a controlled and continuous rate to perform a therapeutic use in warm blooded animals including humans over a prolonged period of time.

Other objects, features and advantages of the invention will be more apparent to those skilled in the art from the following detailed specification, taken in conjunction with the drawings and the accompanying claims.

SUMMARY OF THE INVENTION

This invention concerns an osmotic system for dispensing a beneficial agent to an environment of use. The system is comprised of a semipermeable wall surrounding a compartment and has a passageway through the wall communicating with the compartment and the exterior of the system. The compartment contains (1) an agent that is very soluble in the external fluid and exhibits an osmotic pressure gradient across the wall against the fluid, or, it contains (2) an agent having limited solubility in the fluid that exhibits a limited osmotic pressure gradient across the wall against the fluid. The compartment additionally contains along with (1) or (2) a volume amplifier which amplifier houses a gas generating couple for increasing the delivery of substantially most of the agent at essentially a zero order rate from the compartment. The amplifier is defined as such in that its initial volume is magnified during operation by the gas generating couple through the latter's reaction with water, thereby generating a gas. Optionally, the compartment can contain an osmotically effective compound that exhibits an osmotic pressure gradient across the wall of the device against the fluid as an aid to deliver agent. In operation, agent is released from the system by the combined physico-chemical actions of the system and the volume amplifier comprising fluid being imbibed through the wall into the compartment at a rate controlled by the permeability of the wall and the osmotic pressure gradient across the wall to produce a solution of (1) or a suspension of (2) containing agent and to activate the amplifier to imbibe fluid, generate gas, and expand in volume, whereby the combined actions cause the system to release agent at a controlled rate and continuously over a prolonged period of time.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 1A:
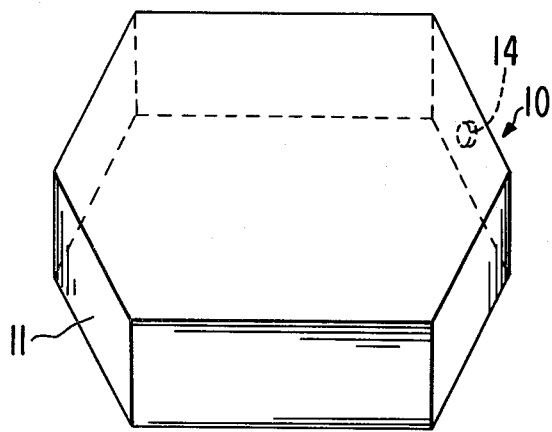
FIG. 1A is a view of an osmotic system designed for orally delivering a beneficial agent.
Figure 1B:
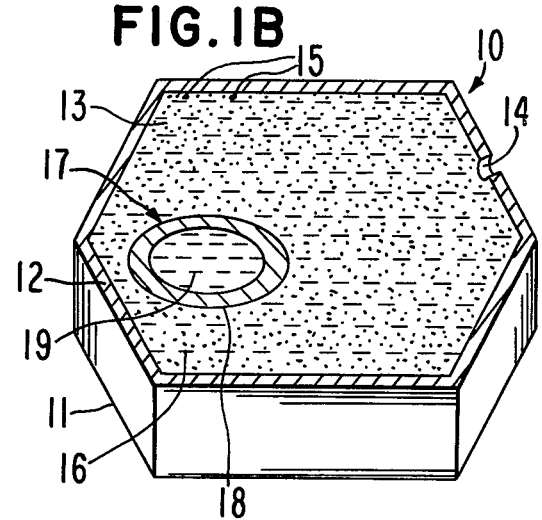
FIG. 1B is a view of the osmotic therapeutic system of FIG. 1A in opened section illustrating the compartment of the system housing a volume amplifier for increasing the amount of the beneficial agent delivered from the system.
Figure 1C:
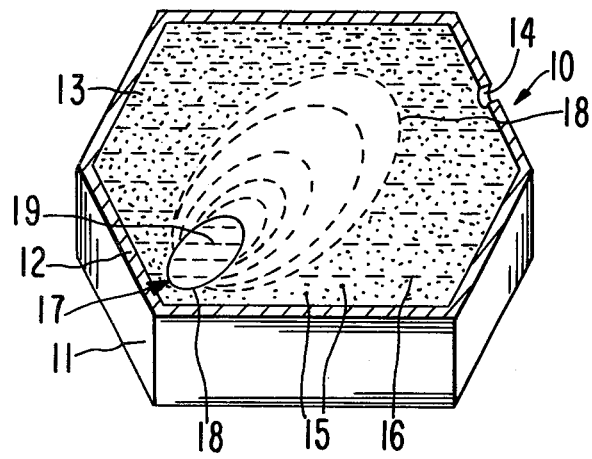
FIG. 1C is a view of the osmotic system of FIG. 1B showing the volume amplifier in operation as it continuously expands in volume and fills the compartment.

Turning now to the drawings in detail, which are examples of various osmotic delivey systems of the invention, and which examples are not to be considered as limiting, one example of an osmotic delivery system manufactured in the form of an osmotic device is indicated in FIGS. 1A, 1B and 1C, considered together, by the numeral 10. The phrases "osmotic delivery system" and "osmotic delivery system in the form of an osmotic device" as used for the purpose of this invention are used as functional equivalents and they also embrace the expressions "osmotic therapeutic system", "osmotic device", and "system".

In FIGS. 1A, 1B and 1C, system 10 is seen comprised of a body 11, having a wall 12, that surrounds a compartment 13, illustrated in FIGS. 1B and 1C in opened section, and a passageway 14 that communicates with compartment 13 and the exterior of system 10. Compartment 13, as seen in FIG. 1B, in one embodiment contains an agent 15 that is soluble in an external fluid and in a presently preferred embodiment is very soluble in the external fluid and exhibits an osmotic pressure gradient across wall 12 against an external fluid. Compartment 13 in another presently preferred embodiment, contains an agent 15 which has limited solubility or is substantially insoluble in the external fluid and exhibits a limited or it does not exhibit any osmotic pressure gradient across wall 12 against said fluid. In still another embodiment, compartment 13 optionally contains a mixture comprising agent 15 which has limited solubility or is substantially insoluble in the fluid mixed with an osmotically effective compound 16 that is soluble in the fluid, and exhibits an osmotic pressure gradient across wall 12 against the fluid, or 15 and 16 are mixed with a suspending compound which compounds further aid in delivering agent 15 from system 10.

System 10 also contains in compartment 13 a volume amplifier 17, seen in FIGS. 1B and 1C, for improving the zero order delivery kinetics of the system 10 and increasing the amount of agent 15 delivered from system 10. Amplifier 17 also identified as component 17, comprises a membrane 18, encapsulating a gas generating couple 19, seen in FIGS. 1B and 1C, which couple is soluble in fluid imbibed into amplifier 17 from fluid in compartment 13. Membrane 18 is free of passageways and it is formed of a material that can move from an initial or rested position, seen in FIG. 1C at 18, through sequential changes as represented by elliptical dotted lines to form amplifier 17 with its membrane in expanded state 18A. Amplifier 17 of the invention is placed in compartment 13 free of any attachment to wall 12, and amplifier 17 can contain one, or a plurality of gas generating couples 19 with each exhibiting the same or different osmotic pressure gradients across membrane 18 against the fluid. In one embodiment, amplifier 17 is placed distant from passageway 14 for urging the maximum amount of agent 15 from compartment 13. This action occurs as amplifier 17 increases in volume and fills compartment 13 thereby urging agent 15 through passageway 14.

Figure 2A:
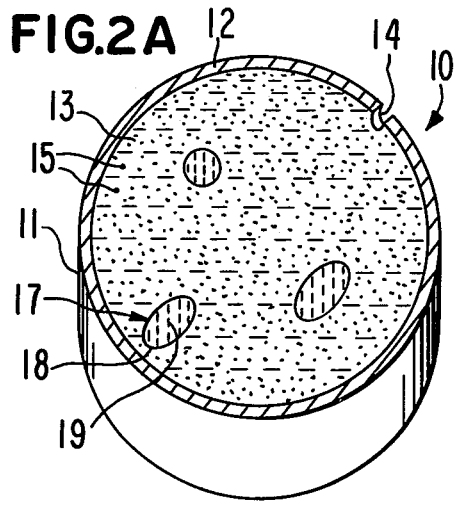
FIG. 2A is another osmotic system in opened section showing the system housing a plurality of gas generating volume amplifiers.
Figure 2B:
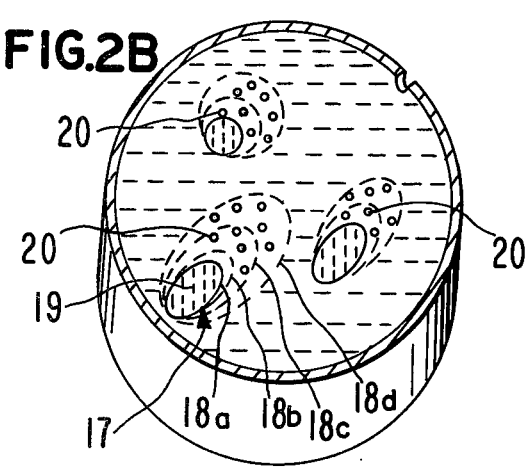
FIG. 2B is a view of FIG. 2A showing the volume amplifier of the invention generating gas and expanding in volume for producing an output of agent of greater magnitude.

In operation when in the environment of use, system 10 releases agent 15 by fluid being imbibed into compartment 13, in a tendency towards osmotic equilibrium at a rate controlled by the permeability of wall 12 and and the osmotic pressure gradient across wall 12 to continuously dissolve agent 15, or form a suspension of agent 15, which is osmotically pumped by amplifier 17 from system 10. Amplifier 17 operates to substantially insure that delivery of agent 15 is constant from system 10 by two methods. First, amplifier 17 operates to concentrate agent 15 by imbibing fluid compartment 13 into amplifier 17 to keep the concentration of agent 15 from falling below saturation; and secondly, amplifier 17 continuously expands in size as the gaseous pressure in 17 increases thereby reducing the volume of compartment 13 and consequently dispensing agent 15 in solution or suspension from compartment 13. Amplifier 17 operates, as seen in FIGS. 2A and 2B, by imbibing fluid into amplifier 17, in a tendency towards osmotic equilibrium at a rate controlled by the permeability of membrane 18 and the osmotic pressure gradient across membrane 18, to continuously wet and dissolve gas generating couple 19 thereby causing it to react and produce a large volume of gas 20. Gas 20, then exerts a gaseous force against membrane 18 thereby expanding membrane 18, as seen in FIG. 2B, through continuously expanding membranes 18a through 18d, whereby agent 15 that is homogeneously or heterogeneously contained in compartment 13 is pushed from compartment 13.

Figure 3:
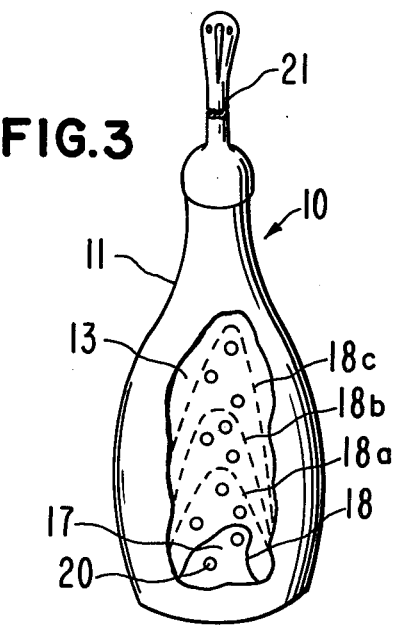
FIG. 3 shows an osmotic system designed for releasing an active agent in the anal canal of an adult.

FIG. 3 represents another osmotic system 10 fabricated according to the invention. System 10, in this embodiment, is designed as a disposable anal therapeutic system comprising an elongated flexible body II manufactured with a dispensing nozzle 21, sized, shaped and adapted for easy insertion into an anal canal, not shown. System 10 of FIG. 3 is structurally identical with system 10 as described above and it has a volume amplifier 17 that generates a gas and operates in a like manner by being capable of increasing in volume from 18 through 18C. System 10 of FIG. 3 contains an agent that when dispensed from system 10 is useful for the management of constipation characterized by fecal impact. System 10, in another imbodiment, can be designed for dispensing an agent in the vagina to produce a local or systemic effect, or it can dispense an odor reductant that emits an odor counteracting scent or fragrance in the vagina, not shown.

While FIGS. 1 through 3 are illustrative of various osmotic delivery systems that can be made according to the invention, it is to be understood these systems are not to be construed as limiting, as the systems can take a wide variety of shapes, sizes, and forms adapted for delivering an agent to different environments of use. For example, the systems include buccal, implant, artificial gland, ocular, cervical, intrauterine, ear, nose, dermal, subcutaneous, and like systems. The systems also can be adapted for delivering an active agent in streams, aquariums, fields, factories, hospitals, veterinary clinics, nursing homes, and other environments of use.

DETAILED DESCRIPTION OF THE INVENTION

In attaining the objects, features and advantages of the invention, it has now been found that semipermeable materials suitable for forming the wall(s) of the system are materials that can form walls, and do not adversely affect the system, the agent, an animal host, or the environment of use. The materials are permeable to the passage of an external fluid, including aqueous and physiological fluids, they are substantially impermeable to agent, volume amplifiers, and other compounds present in the compartment. The materials are of synthetic or naturally occurring origin. Typical semipermeable membranes for forming wall 12 include cellulose acetate, cellulose diacetate, cellulose triacetate, agar acetate, amylose triacetate, beta glucan diacetate, acetaldehyde dimethylacetate, cellulose acetate ethyl carbamate, and other osmosis and reverse osmosis materials including cellulose propionate succinate, methyl cellulose, cellulose acetate p-toluene sulfonate and the like. Exemplary materials also include materials that erode after the system has released its agent in the environment of use. Generally, semipermeable materials useful for forming wall 12 will have a fluid permeability of $10^{-5}$ to $10^{-1}$ (cc.mil/cm$^2$.hr.atm) expressed as per atmosphere of hydrostatic or osmotic pressure difference across wall 12 at the temperature of use. Suitable materials are known in U.S. Pat. Nos. 3,173,876; 3,760,984; 3,845,770; and in 3,916,899.

Membrane 18 of volume amplifier 17 is formed of (1) the above materials and it additionally can contain from 0.01% to 40% of a membrane expansion agent that imparts flexibility, deformability, stretchability and expansion properties to membrane 18 or membrane 18 is formed of (2) a deformable, expandable laminate comprising a semipermeable material laminated to a polymeric deformable, expandable material. Membrane 18 is permeable to the passage of fluid, substantially impermeable to the passage of agent, gas generating compounds and osmotic solutes. These latter properties insure that volume amplifier 17 and membrane 18 operate according to the invention by imparting to amplifier 17 a net rate of increase in volume.

Suitable expansion agents in one embodiment include polyhydric alcohols and derivatives thereof, such as polyalkylene glycols of the formula H—(O-alkylene)-$_n$—OH wherein the bivalent alkylene radical is straight or branched chain and has from 1 to 10 carbon atoms and n is 1 to 500 or higher. Typical glycols include polyethylene glycols 300, 400, 600, 1500, 1540, 4000, and 6000 of the formula H—(OCH$_2$CH$_2$)$_n$—OH wherein n is respectively 5, 5.7, 8.2 to 9.1, 12.5 to 13.9, 29 to 36, 29.8 to 37, 68 to 84, and 158 to 204. Other polyglycols include low molecular weight glycols such as polypropylene, polybutylene and polyamylene.

The membrane expansion agents in another embodiment include poly($\alpha,\omega$)-alkylenediols wherein the alkylene is straight or branched chain of from 2 to 10 carbon atoms such as poly(1,3)-propanediol, poly(1,4-butanediol, poly(1,5)-pentanediol and poly(1,6)-hexanediol. The diols also include aliphatic diols of the formula HOC$_n$H$_{2n}$OH wherein n is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbons atoms such as glycerine, 1,2,3-butanetriol, 1,2,3-pentanetriol, 1,2,4-hexanetriol and 1,3,6-hexanetriol.

Other membrane expansion agents include esters and polyesters of alkylene glycols of the formula HO—(alkylene-O)$_n$—H wherein the divalent alkylene radical includes the straight chain groups and the isometric forms thereof having from 2 to 6 carbons and n is 1 to 14. The esters and polyesters are formed by reacting the glycol with either a monobasic or dibasic acid. Exemplary agents are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid and polyester of triethylene glycol with adipic acid.

Exemplary membrane expansion agents suitable for the present purpose generically include agents that lower the temperature of the second-order phase transition or the glass transition temperature of the membrane forming materials or the elastic modulus thereof, increase the workability of the membrane, its flexibility, and its permeability to fluid. Agents operable for the present purpose include both cyclic and acyclic agents. Typical agents are those selected from the group consisting of phthalates, phosphates, citrates, adipates, tartrates, sebacates, succinates, glycolates, glycerolate, benzoates, myristates, slufonamides, and halogenated phenyls.

Exemplary agents for forming membrane 18 further include dialkyl phthalates, dicycloalkyl phthalates, diaryl phthalates and mixed alkylaryl phthalates as represented by dimethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl clycolate, butyl phthalyl butyl glycolate, ethylene glycol diacetate, ethylene glycol dibutyrate, triethylene glycol diacetate, triethylene glycol dibutyrate and triethylene glycol dipropionate. Also, camphor, N-ethyl-(o- and p-toluene) sulfonamide, chlorinated biphenyl, benzophenone, N-cyclohexyl-p-toluene sulfonamide, and substituted epoxides.

Membrane 18 when optionally manufactured in laminated form is about 0.1 mil to 100 mils thick and is formed of the above membrane forming materials suitably laminated to a laminating forming material such as natural rubber, polyisoprene, polyisobutylene, polybutadiene, butylene-vinyl acetate, ethylene-propylene rubber, para rubber, plantation rubbers, cyclised rubber, reclaimed rubber, and the like, as reported in *Handbook of Common Polymers*, Edited by Scott, J. R., and Roff, W. J., pages 313 to 445, 1976, published by Tinling and Co., Ltd., London. Exemplary laminates formed by laminating a semipermeable material containing an expansion agent to a deformable material include cellulose acetate-polyisoprene, cellulose diacetate-polyisoprene, cellulose acetate butyrate-polybutadiene, cellulose acetate propionate-polybutadiene, cellulose acetate-natural rubber, and the like.

Suitable expansion agents can be selected for blending with the membrane forming materials by selecting agents that have a high degree of solvent power for the materials, are compatible with the materials over both the processing and use temperature range, exhibit permanence as seen by a strong tendency to remain in the membrane, impart the desired properties, and are non-toxic to animals, humans, avians, fishes and reptiles when the osmotic system is used for dispensing drugs. Procedures for selecting an agent having the described characteristics are disclosed in the *Encyclopedia of Polymer Science and Technology*, Vol. 10, pages 228 to 306, 1969, published by John Wiley & Sons, Inc. Procedures for manufacturing laminates are known to the art in U.S. Pat. Nos. 3,600,250; 3,620,898; 3,841,903; 3,855,048; 3,901,232; 3,926,188 and 3,932,693.

The gas generating couple 19 suitable for the purpose of the invention is, in a presently preferred embodiment, an effervescent couple or a composition. The effervescent couple, or composition, comprises at least one preferably solid acidic material and a preferably solid basic material that dissolve and react in an aqueous fluid that enters volume amplifier 17 to produce carbon dioxide effervescent that leads to an increase in volume of 19 for urging agent 15 from system 10. The couple is present in the amplifier 19 in the powder, crystalline, granular, or layered form. The acids that can be used include pharmaceutically acceptable organic acids such as malic, fumaric, tartaric, itaconic, maleic, citric, adipic, succinic and mesaconic, mixtures thereof, and the corresponding anhydride such as itaconic anhydride and citriconic anhydride. Also, inorganic acids can be used such as sulfamic or phosphoric, and the acid disclosed in U.S. Pat. No. 3,325,357. Acid salts such as the salts of organic food can be used including monosodium citrate, potassium acid tartrate and potassium bitartrate. The basic compounds include preferably the pharmaceutically acceptable metal carbonate and bicarbonate salts such as alkali metal carbonates and bicarbonates or alkaline earth carbonates and bicarbonates and mixtures thereof. Exemplary materials include the alkali metals; lithium, sodium, and potassium carbonate and bicarbonate; and the alkaline earth compounds magnesium and calcium carbonate or bicarbonate. Also useful are ammonium carbonate, ammonium bicarbonate, and ammonium sesquecarbonate. The combination of certain of these acids and bases results in a more rapid gas production or effervescence when contacted by water than do other of the above-listed groups. In particular, either citric acid or a mixture of citric acid and tartaric acid and sodium bicarbonate give a rapid gaseous reaction that is useful for quickly increasing the volume of amplifier 17. It will be understood the amount of acidic and basic materials in couple 19 can vary over a wide range to satisfy the amount of effervescence needed to increase the volume of 17. The couple is preferably formed of substantially stoichiometrically balanced parts to produce a combination that generates carbon dioxide. Also, the acid and base materials can be used in any convenient proportion between 1 to 200 parts and 200 to 1 parts on a weight basis to produce the desired results.

Additionally, the gas generating couple includes effervescent couples which form a salt and can hydrate and store up to several moles of water per mole of salt. For these couples, the rate at which gas is produced and the volume increased is controlled by the influx of water imbibed into amplifier 17. Control is effected by hydration of the salt that quenches the chain reaction of gas production caused by the acid base reaction. A water scavenging process can be added to the compartment to fulfill the same function. The gas generating couple also can consist of a single gas producing agent, such as calcium carbide, that evolves a gas on exposure to water. The latter means is particularly useful for non-therapeutic environments.

The expression "passageway" as used herein comprises means and methods suitable for releasing the agent from the system. The expression includes aperture orifice or bore through wall 12 formed by mechanical procedures, or by eroding an erodible element, such as a gelatin plug, in the environment of use. A detailed description of osmotic passageways and the maximum and minimum dimensions for a passageway are disclosed in U.S. Pat. Nos. 3,845,770, and 3,916,899. These patents are assigned to the Alza Corporation of Palo Alto, California, the assignee of this application.

The osmotically effective compounds that can be used for the purpose of the invention include inorganic and organic compounds that exhibit an osmotic pressure gradient against an external fluid across wall 12 and across membrane 18. These compounds are known as osmagents. Generally, an osmagent is needed in compartment 13 when agent 15 has limited solubility in the external fluid and it is needed to imbibe fluid into 13 and form a saturated solution containing agent 15 that is delivered from system 10 by amplifier 17. The osmagents are present in Amplifier 17 for: (a) imbibing fluid from compartment 13 to concentrate a solution or suspension in compartment 13, and (b) for imbibing fluid into amplifier 17 causing it to generate gas, expand in volume and fill compartment 13. The osmagents are used in 13 or 17 by homogenously or heterogenously mixing it, or a mixture of osmagents with with agent 15, or with couple 19, either before they are charged into the 13 or 17, or by self-mixing after they are in 13 or 17. Generally, the presence of an added compound in 17 is superfluous as the gas generating couple, or at least one component of an effervescent couple, for example sodium bicarbonate, will exhibit an osmotic pressure gradient. In those applications, when the couple exhibits a limited osmotic pressure gradient, an osmotically effective compound is mixed therein. Osmotically effective compounds useful for the present purpose include inorganic and organic salts and polysaccharides such as magnesium sulfate, magnesium chloride, sodium chloride, lithium chloride, potassium sulfate, sodium carbonate, sodium sulfate, lithium sulfate, potassium chloride, calcium bicarbonate, sodium sulfate, calcium sulfate, potassium acid phosphate, calcium lactate, tartaric acid, lactose, fructose, mannitol, sorbitol, and mixtures thereof. The compound is initially present in excess and it can be in particle, crystal, pellet, powder, or granule form. The osmotic pressure can be measured with a commercially available osmometer identified as Vapor Pressure Osmometer, Model 2B, available from Hewlett-Packard, Avondale, Penna. The osmotic pressure II, in atmospheres ATM, of the osmagents suitable for the invention will be greater than zero ATM, generally from zero ATM up to 500 ATM, or higher.

The expression "active agent" as used herein broadly includes any compound, composition of matter or mixture thereof, that can be delivered from the system to produce a beneficial and useful result. Agent 15 can be soluble or very soluble in a fluid that enters the compartment and functions as its own osmotically effective solute, it can be very slightly soluble or practically insoluble in the fluid and be optionally mixed with an osmotically effective compound soluble in fluid that in either instance is delivered from system 10 by amplifier 17. The active agent includes pesticides, herbicides, germicides, biocides, algicides, rodenticides, fungicides, insecticides, anti-oxidants, plant growth promotors, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promotors, air purifiers, micro-organism, attenuators, and other agents that benefit the environment of use.

In the specification and the accompanying claims, the term "drug" includes any physiologically or pharmacologically active substance that produces a localized or systemic effect or effects in animals, including warm blooded animals, mammals, humans, primates, avians, domestic household animals, sport and farm animals such as sheep, goats, cattle, horses and pigs, for administering to laboratory animals such as mice, rats and guinea pigs, and to fishes, reptiles, jungle and zoo animals. The active drug that can be delivered includes inorganic and organic compounds without limitation, those materials that act on the central nervous system such as hypnotics and sedatives, psychic energizers, tranquilizers, antidepressants, anticonvulsants, muscle relaxants, antiparkinson agents, analgesics, anti-inflammatory, local anesthetics, muscle contractants, anti-infectives, anti-microbials, anti-malarials, hormonal agents, sympathomimetics, metabolic aberration correcting agents, diuretics, anti-parasitics, neoplastics, hypoglycemics, nutritionals, fats, ophthalmic, electrolytes, cardiacs, and diagnostic agents.

Exemplary of drugs that are very soluble in water and can be delivered by the systems of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methscopolamine bromide, isopropamide iodide, tridihexethyl chloride, phenformin hydrochloride, and methylphenidate hydrochloride.

Exemplary of agents that are very slightly soluble or practically insoluble in water that can be delivered by the system of this invention include diphenidol, meclizine hydrochloride, prochlorperazine maleate, thielthylperazine maleate, anisindione, diphenadione, erythrityl tetranitrate, dizoxin, isoflurophate, reserpine, acetazolamide, methazolamide, bendroflumethiazide, chlorpropamide, tolazamide, chlormadinone acetate, phenaglycodol, allopruinol, aluminum aspirin, methotrexate, acetyl sulfisoxazole, erythromycin, steroids, including corticosteroids such as hydrocortisone, desoxycorticosterone acetate, cortisone acetate, triamcinolone, androgens such as methyltestosterone, estrogenic steroids such as 17B-estradiol, and ethinyl estradiol, progestational steroids such as 17α-hydroxyprogesterone acetate, 19-nor-progesterone, prednisolone, norethindrone acetate, progesterone, norethynodrel, and the like.

Exemplary active drugs that can be dispensed by systems manufactured for gastrointestinal administration and having shapes and sizes such as round with a diameter of 3/16 inch to ½ inch, or shaped like a capsule having a range of sizes from triple zero to zero, and from 1 to 8, include gastrointestinal drugs such as bismuth subcarbonate that is practically insoluble in water, nylidrin hydrochloride having a solubility of 1 gm dissolving in 65 ml of water, physotigmine salicylate having a solubility of 1 gm dissolving in 75 ml of water, antimuscarinus such as mepenzolate bromide having a solubility of 1 gm dissolving in 112 ml of water, carbonic anhydrase inhibitors such as acetazolamide, dichlorphenamide and methazolamide all being very slightly soluble in water, and other drugs whose solubility is set forth in *Pharmaceutical Science*, by Remington, 15 Ed., 1975, published by Mack Publishing Co., Easton, Penna. Additionally, the systems can be used for dispensing other drugs whose solubility is set forth in *Merck Index*, Eighth Edition, 1968, published by Merck & Co., Rahway, New Jersey. Other drugs include analgesics such as aspirin, salicylamide, salicylic acid, sodium salicylate, choline salicylate, acetaminophen, phenacetin, codeine and morphone; antimicrobials such as penicillin, tetracycline, oxytetracycline, chloramphenicol and sulfonamides; hormonal agents such as prednisolone, cortisone, cortisol, 17β-estradiol, α-estradiol, estriol, progesterone, 19-nor-pregn-4-ene-3,20-dione and 17-ethinyl-17-hydroxy-5(10)-estren-3-one with ethynylestradiol 3-methyl ether; hypoglycemic drugs such as tolbutamide, acetohexamide, tolazamide and chlorpropamide; nutritional agents such as ascorbic acid, niacin, nicotinamide, folic acid, choline, biotin, pantothenic acid, vitamin $B_{12}$, essential amino acids and essential fats, and electrolytes such as calcium gluconate, calcium lactate, potassium chloride, sodium chloride, potassium fluoride, ferrous compounds such as ferrous fumarate, ferrous citrate, ferrous carbonate, ferrous gluconate, ferrous sulfate, and sodium lactate.

The drug also can be in various forms, such as uncharged molecules, molecular complexes, pharmacologically acceptable acid or base addition salts such as hydrochlorides, hydrobromides, sulfate laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides can be used alone or mixed with other drugs. Also, a drug that is water insoluble can be used in a form that on its release from the device, is converted by enzymes, hydrolyzed by body pH or other metabolic processes to the original form, or to a biologically active form. The agent or drug can be in the compartment as a dispersion, paste, cream, particle, granule, emulsion, suspension or powder. Also, the agent or drug can be mixed with a binder, diluent, dispersant, stabilizer, emulsifier or wetting agent and dyes.

The amount of agent present in the system is initially in excess of the amount that can be dissolved in or mixed with the fluid that enters the compartment. Under this physical state when the agent is soluble and in excess, or if the agent is mixed with an osmagent, the system will osmotically operate in cooperation with the amplifier to give a substantially constant rate of release. The rate of agent release pattern can also be varied by having different amounts of agent in the compartment to form solutions, suspensions or mixtures containing different concentrations of agent, and optionally, osmagents for delivery of agents from the system. Generally, the system can house from 0.05 ng to 5 grams or more of agent, with individual systems containing for example, 25 ng, 1 mg, 5 mg, 250 mg, 500 mg, 1.5 g of agent or mixtures thereof, and the like. The beneficial drugs are known to the art in *Pharmaceutical Sciences,* by Remington, 15th Ed., 1975, published by Mack Publishing Co., Easton Penna; *The Drug, The Nurse, The Patient, Including Current Drug Handbook,* 1974–1976, by Falconer, et al, published by Saunder Company, Philadelphia, Penna; and *Medicinal Chemistry,* 3rd Ed., Vol. I & II, by Burger, A., published by Wiley-Interscience, New York.

The solubility or insolubility of an agent in an external fluid can be determined by various art known techniques. One method consists of preparing a saturated solution or suspension comprising the external fluid plus the agent in suspension and ascertaining by analyzing the amount of agent presently dissolved in a definite quantity of the fluid. A simple apparatus for this purpose consists of a test tube of medium size fastened upright in a water bath maintained at a constant temperature and pressure in which the fluid and agent are placed and stirred by a motor. After a given period of stirring, a definite volume of the filtered fluid is analyzed and the stirring continued for an additional period of time. If the analysis shows no increase of dissolved agent after successive periods of stirrings, in the presence of excess solid agent in the fluid, the solution or suspension is saturated and the solubility in the fluid is taken as the mass of agent per unit volume of solubility. Optionally, if the agent is soluble an osmagent is not needed; if the agent has limited solubility or if it is insoluble in the fluid, then an osmagent can optionally be incorporated into the compartment already housing the delivery component. Numerous other methods are available for determining the solubility of an agent in a fluid. Typical methods used for measuring solubility include chemical analysis, ultraviolet spectrometry, density, refractive index and electrical conductivity. Generally, for the purpose of this invention soluble to very soluble agents will dissolve in the range of from 175 mg to 900 mg of agent or higher per milliliter of fluid, and very slightly soluble to practically insoluble agents will dissolve in the range of 0.001 mg to 125 mg of agent per milliliter of fluid. While the invention has been described with particular reference to presently preferred embodiments including soluble and insoluble, it is understood the system of the invention can be used to deliver other agents having other degrees of solubilities. Details of various methods for determining solubilities are described in *United States Public Health Service Bulletin,* No. 67 of the Hygenic Laboratory; *Encyclopedia of Science and Technology,* Vol. 12, pages 542 to 556, 1971, published by McGraw-Hill, Inc.; and *Encyclopedic Dictionary of Physics,* Vol. 6, pages 547 to 557, 1962, published by Pergamon Press, Inc.

The systems of the invention are manufactured by standard techniques. For example, in one embodiment, the agent, the volume amplifier, and other ingredients that may be housed in the compartment and a solvent are mixed into a solid, semi-solid or gel by conventional methods such as ballmilling, calendering, stirring or rollmilling and then pressed or tabletted into a preselected shape. The wall forming the system can be applied by molding, spraying or dipping the pressed shape into wall forming materials. In another embodiment, a wall can be cast, shaped to the desired dimensions to define a wall that surrounds a compartment that is filled with agent and volume amplifier and then closed. The system also can be manufactured with an empty compartment that is filled through the passageway. Walls forming the system also can be joined by various joining techniques such as high frequency electronic sealing that provides clean edges and firmly formed walls. Another, and presently preferred technique that can be used is the air suspension procedure. This procedure consists of suspending and tumbling the agent and amplifier in a current of air and a wall forming composition until the wall is applied to the agent and amplifier. The amplifier comprising the membrane surrounding the gas generating couple can be manufactured by the above techniques. Also, the air suspension procedure is well-suited for independently forming the amplifier by applying a membrane to the couple. The air suspension procedure is described in U.S. Pat. No. 2,799,241; in *J. Am. Pharm. Assoc.,* Vol. 48, pages 451 to 459, 1959; and ibid., vol. 49, pages 82 to 84, 1960. Other wall forming and membrane forming techniques such as pan coating can be used in which the materials are deposited by successive spraying of the polymer solution on the agent or osmagent tumbling in a rotating pan. Other standard manufacturing procedures are described in *Modern Plastics Encyclopedia,* Vol. 46, pages 62 to 70, 1969; and in *Pharmaceutical Sciences,* by Remington, 14th Ed., pages 1626 to 1678, 1970, published by Mack Publishing Company, Easton, Penna.

Exemplary solvents suitable for manufacturing the wall, or the membrane, include inert inorganic and organic solvents that do not adversely harm the wall forming materials, the membrane forming materials, and the final system. The solvents broadly include members selected from the group consisting of aqueous solvents, and organic solvents, such as alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toulene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. In addition wall forming materials can be formed from latacies.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery system for the controlled and continuous release of a beneficial drug to a biological environment of use was constructed as follows: first, a volume amplifier was manufactured by encapsulating in an air suspension machine a gas generating couple. The couple weighed 169 mg and it consisted of a homogenous, pressed mixture of 56.7% potassium hydrogen carbonate, 40.2% citric acid and 3% anhydrous magnesium silicate. The couple was surrounded with a membrane consisting of 90% cellulose acetate having an acetyl content of 32% having homogenously dispersed therein 10% by weight of polyethylene glycol having a molecular weight of 400. The encapsulation was carried out with a solvent consisting of methylene chloride methanol, 80:20, volume:volume, until each couple was encapsulated with the membrane.

Next, the couple was coated with 671 mg of dry potassium chloride, which was pressed in a manesty tableting maching and finally coated with a semipermeable wall. The wall consists of semipermeable cellulose acetate having an acetyl content of 32%, and it was formed from a 5% w/w solution in acetone:water in the proportion of 89:11 wt/wt. An osmotic passageway was drilled through the wall and it had a diameter of 7.8 mils to yield the osmotic system.

EXAMPLE 2

The procedure of Example 1 is repeated in this example, with all conditions as described, except that the osmotic system is manufactured with the potassium chloride in the compartment replaced with a drug selected from the group consisting of sodium phenobarbitol, salicylamide, acetazolamide sodium and magnesium sulfate.

EXAMPLE 3

An osmotic therapeutic system manufactured in the form of an oral, osmotic device for delivering procainamide hydrochloride to the gastrointestional tract of a warm blooded mammal is manufactured as follows: first, a mixture of 25 mg of citric acid, 45 mg of sodium bicarbonate and 0.125 mg of monocalcium phosphate dibasic, is coated in an air suspension machine with a membrane forming composition comprising (1) 70% cellulose acetate having an acetyl content of 32% mixed with (2) 30% polyethylene glycol having a molecular weight of 400 dissolved in (3) methylene chloride-methanol, 80:20, until the mixture is encapsulated with the membrane to form volume amplifier 17. Next, 235 mg of procainamide hydrochloride having a molecular weight of 271.79 is pressed into a solid mass having a shape corresponding to the shape of the amplifier and joined thereto by spreading a drop of liquified cellulose acetate between their interfaces. Then, the just-formed composite is coated in an air suspension machine with a wall of semipermeable polymeric cellulose acetate having an acetyl content of 32%. The cellulose acetate is intimately applied from a 5% w/w solution in acetone:water in the proportion of 89:11 wt/wt. Finally an osmotic passageway is drilled through the wall, at a point distant from the amplifier, into the compartment containing the procainamide hydrochloride to yield the osmotic system. The passageway has a diameter of 8.1 mils.

EXAMPLE 4

The procedures of Examples 1 through 3 are repeated in this example with all conditions as previously described except that the useful agent in the compartment is replaced with a member selected from the group consisting of hypnotics, sedatives, psychic energizers, tranquilizers, anticonvulsants, muscle relaxants, antiparkinson agents, anti-inflammatory, anesthetics, muscle contractants, anti-microbials, anti-malarials, hormones, sympathomimetics, diuretics, hypoglycemics, and nutritional agents.

EXAMPLE 5

The procedure of Example 4 is repeated in this example and all conditions are as described except that the compartment also houses an osmagent selected from the group consisting of mannitol, ammonium chloride, and a mixture of sodium chloride and ammonium chloride, and sorbitol.

EXAMPLE 6

The procedure of Examples 4 and 5 are repeated in this example, with all conditions as described except that the compartment contains a member selected from the group consisting of prochlorperazine edisylate, ferrous sulfate, aminocaproic acid, mecamylamine hydrochloride, amphetamine sulfate, benzphetamine hydrochloride, isoproternol sulfate, methamphetamine hydrochloride, phenmetrazine hydrochloride, bethanecol chloride, methacholine chloride, atropine sulfate, methscopolamine bromide, isopropamide iodide, tridihexethyl chloride, phenformin hydrochloride and methylphenidate hydrochloride.

EXAMPLE 7

An osmotic system manufactured in the form of an osmotic delivery device is made as follows: first, a volume amplifier shaped like a tablet weighing 200 mg comprising a combination of 113.4 mg of sodium bicarbonate, 70 mg of citric acid, 10 mg of glycine, 2 mg of magnesium stearate and 1 mg of talc is pressed in a conventional manesty press and then coated with a membrane forming composition consisting of 70% cellulose acetate having an acetyl content of 32% and 30% polyethylene glycol having a molecular weight of 400. The amplifier had a diameter of 5/16 inch, an area of 1.5 cm$^2$, the expandable membrane had a thickness of 4.0 mils. Next, 225 mg of a composition comprising 210 mg of procainamide hydrochloride, 11 mg of poly(vinyl pyrrolidone) and 4 mg of magnesium stearate are tableted around the amplifier until the tableted mass had a diameter of 7/16 inch, a thickness of 4.82 mm, a final volume of 0.355 cm$^3$ with the procainamide hydrochloride having a volume of 0.218 cm$^3$. Next, the procainamide hydrochloride volume amplifier composite is coated with a 4 mil thick wall of a wall-forming composition consisting of 90% cellulose acetate having an acetyl content of 38.3% and 10% polyethylene glycol having a molecular weight of 400. Finally, a passageway having a diameter of 10 mils is drilled through the wall to yield the osmotic system.

EXAMPLE 8

The procedure of Example 7 is repeated in this example with all conditions as described except that the drug in the present example is a member selected from the group consisting of diphenidol, meclizine hydrochloride, prochlorperazine maleate, ethinyl estradiol, progesterone, erythrityl tetranitrate, acetazolamide, methazolamide, aspirin and allopurinol. The drugs delivered by the osmotic system manufactured according to the example are in another embodiment present in the compartment in a formulation consisting of 20% drug, 9% sorbitol, 20% pectin, 1% magnesium stearate and a trace of non-toxic yellow dye, and the membrane of the volume amplifier is made of a rubber polyurethane with substantially water permeability.

EXAMPLE 9

The procedure of Examples 7 and 8 are repeated in this example with the conditions as set forth with the added proviso that the gas generating couple is an effervescent couple containing a member selected from the group consisting of malic, fumaric, tartaric itaconic, maleic, adipic, succinic, mesaconic and glycine pharmaceutically acceptable acids, and a member selected from the group consisting of potassium carbonate, calcium carbonate, magnesium carbonate, sodium bicarbonate, potassium bicarbonate, magnesium bicarbonate, calcium bicarbonate, and mixtures thereof.

EXAMPLE 10

A laminate consisting of a pair of laminas is manufactured as follows: first, a thin, 1 to 10 mil thick lamina of cellulose acetate having an acetyl content of 32% and dispersed in a solvent consisting of 80% methylene chloride and 20% methanol is cast onto a thin, 1 to 10 mil thick lamina consisting of synthetic colorless, transluscent, isoprene rubber. The isoprene lamina becomes slightly tacky in the presence of the solvent causing the cellulose acetate lamina to stick thereto. Next, the solvent is evaporated at 50° C. under vacuum. The final laminate is 2 to 10 mils thick.

The novel osmotic system of this invention uses a volume amplifier for the obtainment of precise release rates and enhanced delivery of agent to environments of use while simultaneously maintaining the integrity and character of the system. And, while there has been described and pointed out features of the invention as applied to presently preferred embodiments, those skilled in the art will appreciate that various modifications, changes, additions and omissions in the system illustrated and described can be made without departing from the spirit of the invention.

I claim:

1. An osmotic system for the controlled delivery of a beneficial agent to an environment of use, said system consisting essentially of:
   (a) a shaped wall permeable to the passage of an external fluid present in the environment of use and substantially impermeable to the passage of agent, the wall surrounding and forming;
   (b) a compartment having a single internal space;
   (c) an agent formulation in the compartment that exhibits an osmotic pressure gradient across the wall against the external fluid;
   (d) a volume amplifier in the compartment for increasing the amount of agent delivered from the compartment, said amplifier consisting essentially of an expandable semipermeable membrane surrounding a gas generating couple, said couple consisting essentially of an acidic component and a basic component that in a fluid environment react and generate a gas;
   (e) a passageway in the wall that communicates with the interior of the compartment and the exterior of the system for delivering agent from the system; and,
   (f) wherein in operation, when the system is in the environment of use, fluid from the environment is imbibed through the wall into the compartment in a tendency towards osmotic equilibrium at a rate determined by the permeability of the wall and the osmotic pressure gradient across the wall, which fluid (1) forms a composition containing agent formulation, and (2) activates the amplifier to imbibe fluid from within the compartment, said fluid wetting the couple in the amplifier causing it to react, generate gas and increase the volume of the amplifier, urging it to expand and continuously fill the compartment, whereby through the combined action of (1) and (2) agent is delivered through the passageway from the system at a controlled rate over a prolonged period of time.

2. The osmotic system for delivering a beneficial agent according to claim 1, wherein the compartment contains an osmotically effective compound that exhibits an osmotic pressure gradient across the wall against the external fluid.

3. The osmotic system for delivering a beneficial agent according to claim 1, wherein the acidic component in the volume amplifier is a member selected from the group consisting of malic, fumaric, tartaric, itaconic, maleic, citric, adipic, succinic, measoconic, glycine and mixtures thereof, and wherein the basic component in the volume amplifier is a member selected from the group consisting of sodium carbonate, potassium carbonate, calcium carbonate, magnesium carbonate, sodium bicarbonate, potassium bicarbonate, magnesium bicarbonate, calcium bicarbonate, and mixtures thereof.

4. The osmotic system for delivering a beneficial agent according to claim 1, wherein the volume amplifier membrane is free of passageways and the membrane contains an expansion agent that imparts flexibility and expandability to the membrane, which expansion agent is a member selected from the group consisting of poly-($\alpha,\omega$) alkylenediol, polyester alkylene glycol, and polyalkylene glycol.

5. The osmotic system for delivering a beneficial agent according to claim 1, wherein the system is sized, shaped and adapted for administering a beneficial agent to the gastrointestinal tract, and the beneficial agent is a drug.

6. The osmotic system for delivering a beneficial agent according to claim 1, wherein the rate of imbibition by the volume amplifier is determined by the permeability of the volume membrane and the osmotic pressure gradient across the volume amplifier membrane against fluid present in the compartment, and wherein the rate of increase in volume of the amplifier corresponds to the rate of imbibition of the amplifier and the volume of gas generated within the amplifier.

7. The osmotic system for the controlled delivery of a beneficial agent according to claim 1, wherein the compartment houses a multiplicity of volume amplifiers.

8. The osmotic system for the controlled delivery of a beneficial agent according to claim 1, wherein the volume amplifier in the compartment is positioned distant from the passageway in the wall, and in operation it expands and continuously fills the compartment for delivering the maximum amount of beneficial agent through the passageway, and the composition formed is a solution.

9. The osmotic system for the controlled delivery of a beneficial agent according to claim 1, wherein the couple in the amplifier when brought into fluid reactive contact generates carbon dioxide within the volume amplifier, and the composition formed in the compartment is a suspension.

10. The osmotic system for the controlled delivery of a beneficial agent according to claim 1, wherein the wall of the osmotic system is a semipermeable polymer selected from the group consisting of cellulose acetate, cellulose diacetate, cellulose triacetate, polyamide and polyurethane.

11. The osmotic system for the controlled delivery of a beneficial agent according to claim 1, wherein the volume amplifier has an expandable membrane that contains a member selected from the group consisting of cellulose acetate, cellulose esters, cellulose ethers, polyurethane, and polyamide.

12. The osmotic system for delivering a beneficial agent according to claim 1, wherein the agent is a pharmaceutically acceptable drug selected from the group consisting of central nervous system, hypnotic, sedative, antidepressant, tranquilizer, anticonvulsant, antiparkinson, analgesic, anti-inflammatory, anesthetic, anti-infective, hormonal, sympathomimetic, diuretic, hypoglycemic, cardiac, and ophthalmic.

13. The osmotic system for the controlled delivery of a beneficial agent according to claim 1, wherein the environment of use is the anus and the system is sized, shaped and designed for insertion and delivery of agent in the anus.

14. The osmotic system for the controlled delivery of a beneficial agent according to claim 1, wherein the environment of use is the anus, the system is sized, shaped and adapted for insertion in the anus, and it is useful for the management of constipation characterized by fecal impact.

15. The osmotic system for the controlled delivery of a beneficial agent according to claim 1, wherein the environment of use is the vagina, the system is sized, shaped and adapted for use in the vagina, and the osmotic system and volume amplifier maintain their physical and chemical integrity during the prolonged period of agent delivery from the system.

* * * * *